United States Patent [19]
James et al.

[11] Patent Number: 5,763,238
[45] Date of Patent: Jun. 9, 1998

[54] BORONIC ACID COMPOUND HAVING A BINAPHTHYL GROUP

[75] Inventors: Tony James; Saman Sandanayake, both of Kurume; Seiji Shinkai, Fukuoka, all of Japan

[73] Assignee: Research Development Corporation of Japan, Saitama, Japan

[21] Appl. No.: 580,307

[22] Filed: Dec. 28, 1995

[51] Int. Cl.$^6$ .......................................... G01N 21/76
[52] U.S. Cl. .............................. 436/172; 562/7; 436/546; 252/301.16
[58] Field of Search ................................. 562/7; 436/172, 436/546; 252/301.16

[56] References Cited

FOREIGN PATENT DOCUMENTS 3720736  1/1989  Germany .

Primary Examiner—Samuel Barts
Attorney, Agent, or Firm—Wenderoth, Lind & Ponack

[57] ABSTRACT

This invention relates to novel chiral boronic acid compounds which are capable of binding to polyols, particularly to saccharides and are useful in the analysis or separation of diols.

7 Claims, 2 Drawing Sheets

BORONIC ACID COMPOUND HAVING A BINAPHTHYL GROUP

FIELD OF THE INVENTION

The present invention relates to a boronic acid compound, and particularly to a novel chiral boronic acid compound capable of binding to polyols, particularly to saccharides, which compound is suitable for use in analysis or separation of the diols.

BACKGROUND OF THE INVENTION

Polyols, as typified by saccharides, widely occur in nature and play an important role in living organisms. They are also one of the key materials used in industry. Polyols are characterized by their complexity and variety. In particular, a saccharide is composed of the D-form and L-form, which are known as optical isomers. The separation of such isomers (optical solution) is of great importance in many fields, such as in synthesizing pharmaceutical substances. The contamination by an undesired optical isomer may cause not only a lowering of the pharmaceutical efficacy but also serious side-effects in the patient. However optical isomers are difficult to selectively isolate or detect, since they have identical physical properties such as boiling point and melting point. If it should be possible to selectively detect or isolate a polyol of a specific structure, that is, to selectively detect or isolate the D-form or L-form of isomers, it would not only make a great contribution to the world of science but also arouse a variety of industrial applications. However, no practical measures seem to be available for this purpose.

SUMMARY OF THE INVENTION

One possible approach for the separation and/or analysis of polyols such as saccharides would be the utilization of a substance capable of selectively binding to a target polyol in which the binding can be externally read out.

It is well known that a boronic acid group, $B(OH)_2$, covalently reacts with OH groups present in such compounds as saccharides. Based on this phenomenon, the present inventors previously created a novel phenylboronic acid compound which emits strong fluorescence when combined with glucose (Japanese Patent Application No.147061/1994). While the compound is suitable for use in the detection of a specific saccharide, it is unable to discriminate between the D-form and L-form of the saccharide.

The present inventors have now succeeded in synthesizing for the first time a novel boronic acid compound which is able to discriminate between the D-form and L-form of a saccharide when necessary.

Thus, according to the present invention there is provided a novel chiral boronic acid compound having a binaphthyl group which can be expressed by the following general formula(1):

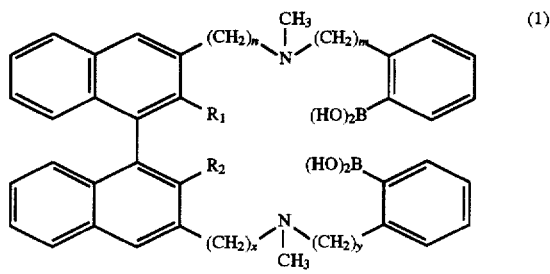

In the formula(1), $R_1$ and $R_2$ are generally the same, but may be different. $R_1$ and $R_2$ are selected from the group consisting of alkoxy groups having 1 to 4 carbon atoms and OH (hydroxyl group), with methoxy, ethoxy or OH being particularly preferred.

In the above formula(1), n+m is 2 or 3 and x+y is 2 or 3, in which each of n, m, x and y may be zero. n and x are generally the same but may be different. m and y are generally the same but may be different. Most generally, each of n, m, x and y is 1. Thus, a preferred example of the compounds falling within the definition of the formula(1) can be expressed by the following formula(2):

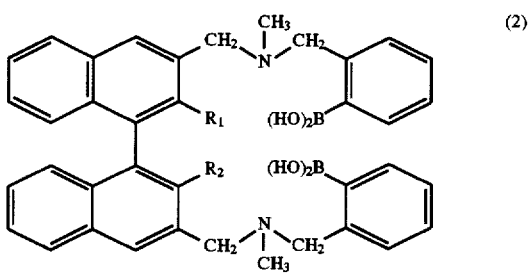

The boronic acid compound having a binaphthyl group of the present invention as expressed by the aforesaid formulas (1) and (2) has a chiral structure, i.e. a mirror-image (enantiomer) structure consisting of R-form (R-isomer) and S-form (S-isomer). Thus, the formula(1) (or formula(2)) expresses either R-form or S-form of the compound. The boronic acid compound of the present invention is characterized by the fact that the R-form and S-form thereof each exhibits an extremely high selectivity to one of the enantiomers of a polyol, particularly of a saccharide.

Specifically, the R-form of the boronic acid compound of the following formula(3) has a high selectivity to D-form of a monosaccharide such as glucose and fructose, and emits an increased fluorescence upon binding to such D-form, while the S-form of the same compound exhibits a high selectivity to L-form of the monosaccharide and emits an increased fluorescence upon binding to the L-form.

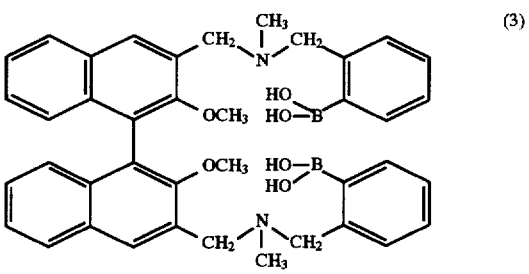

Thus, a boronic acid compound having a binaphthyl group of the present invention can be used for the separation and analysis of a specific polyol including saccharides since it is capable of binding to such polyol where the binding with the polyol can be read out as fluorescence. The binding between the polyol (saccharide) and the fluorescent compound can easily be cleaved by changing the pH of the system through an appropriate acid, thereby restoring the saccharide.

Analysis or detection of polyols (saccharides) may be conveniently carried out with a kit composed of the above-mentioned boronic acid compound(s). Thus, another aspect of the present invention provides a saccharide-detecting kit comprising the R-form and/or S-form of a fluorescent compound defined by any of the aforesaid formulas in a solid (powdery) or crystalline state, a buffer solution and a set of standard solutions. The standard solutions are varied concentrations of the saccharide to be detected. The calibration of a spectrophotometer for the detection is conducted by dissolving the compound of the invention in the standard solutions with the buffer solution and measuring fluorescent intensity against varied saccharide solutions. Thus, in the detection of D-glucose or D-fructose, for example, such a kit composed of the R-form of the compound of the formula(3) is effectively utilized. On the other hand, a kit composed of the S-form of the compound(3) is effective for detecting L-glucose or L-fructose. Furthermore, the compounds of the present invention can be applied to the detection of a racemic mixture. For example, in the detection of a racemic mixture of D-glucose and L-glucose, a kit composed of R-form and/or S-form of the compound of the formula(3) is used in which the fluorescent intensity of the R-form of the compound increases with increasing D-glucose and decreases with increasing L-glucose, and vice versa for the S-form of the same compound.

As another embodiment, the compound of the present invention may be used in a chromatographic detection method for saccharide. The compound is carried on an appropriate support and packed in a column. When a saccharide-containing sample passes through the column, a complex will form between the compound and the saccharide emitting fluorescence measurable by a suitable means.

Figure 1:
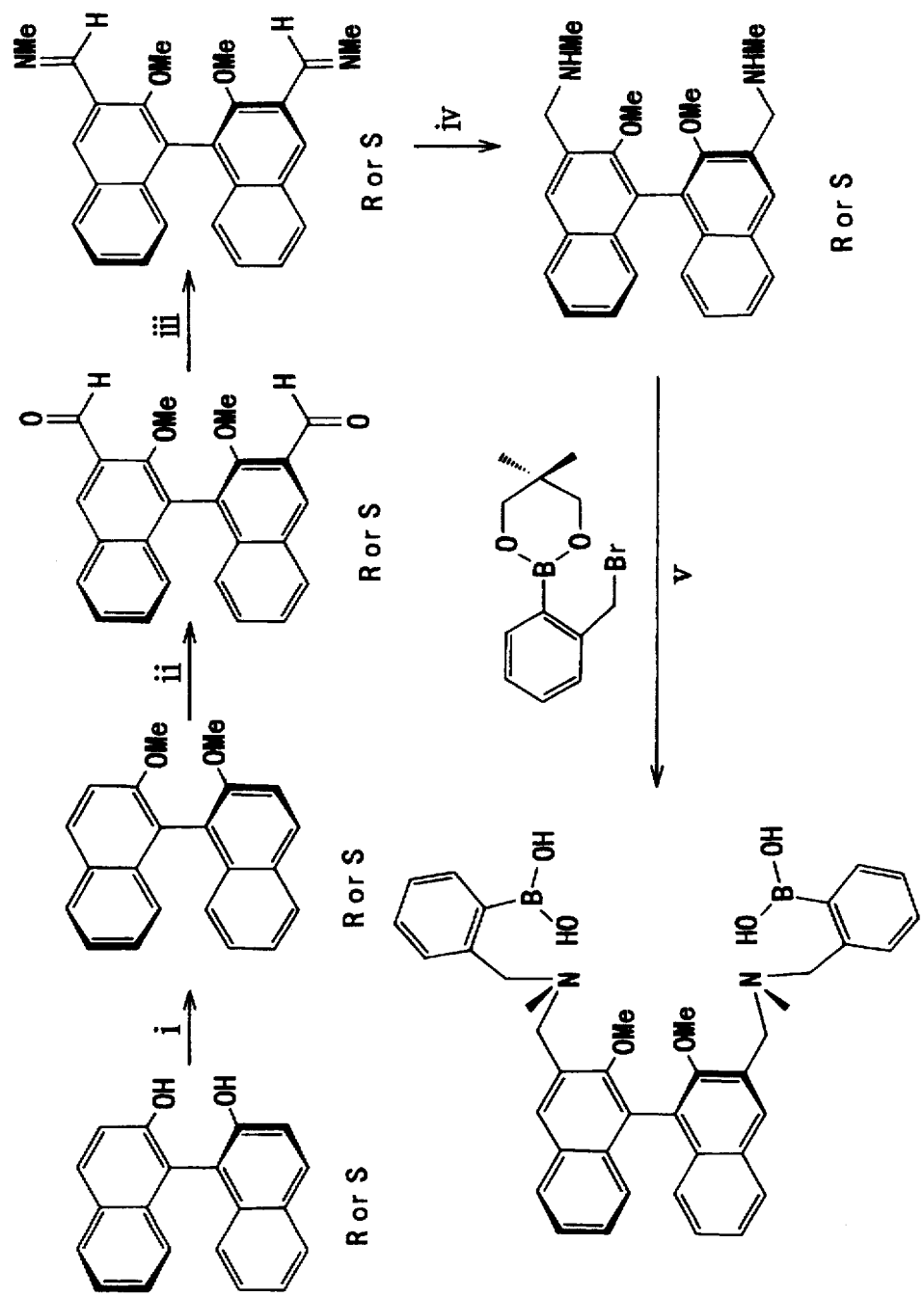
FIG. 1 is a scheme illustrating the synthesis of a boronic acid of the present invention, in which Me represents methyl.

The boronic acid compound can be prepared by synthetic routes as exemplified in FIG. 1, in which each of n, m, x and y is 1. In the chemical formulas herein provided including those in FIG. 1, carbon atoms and hydrogen atoms are not shown as conventionally done.

Referring to FIG. 1, the OH groups at the 1 and 1' positions of binaphthol (commercially available) are alkoxylated. The alkoxylation may be conducted, in the presence of an alkali such as potassium carbonate, using methyl iodide in the case of $R_1$ and $R_2$ being methoxy as in FIG. 1, and using ethyl bromide, propyl bromide and butyl bromide in the case where both $R_1$ and $R_2$ are ethoxy, propoxy and butoxy groups, respectively (route i). The route(i) is omitted when $R_1$ and $R_2$ are OH.

Then, the 3 and 3' positions of the resulting compound are formylated in the manner as detailed later in the working example (route ii), followed by the formation of a Schiff's base using methylamine (route iii). The imine thus obtained is allowed to react with $NaBH_4$ to form 3,3'-bis(N-methylaminomethyl) derivative (route iv). Finally, an alkylation reaction is conducted using 2-bromomethylphenyl boronic acid (protected with 2,2'-dimethyl-1,3-propanediol) to form the desired boronic acid having a naphthyl group (route v).

The invention will now be illustrated by the following examples, which are not for restricting the invention.

EXAMPLE 1

The compound of the above-mentioned formula, i.e., a boronic acid compound falling within the general formula(2) in which $R_1=R_2$=methoxy, was prepared by the synthetic routes (i) to (iv) as shown in FIG. 1.

(i) 25 g of R- or S-binaphthol, commercially available from Tokyo Kasei Co. (Tokyo, Japan), 24.6 g of methyl iodide and 24.1 g of potassium carbonate in 500 ml of acetone were refluxed for 3 days. After the solvent was removed, the solid was extracted with dichloromethane/water. The organic layer was then washed with water (3×200 ml) to obtain the desired dimethylether.

(ii) 20 g of the dimethylether of R- or S-binaphthol and 31.2 ml of TMEDA (tetramethylethylenediamine : 1,2-bis(dimethylamino)ethane) were mixed in 400 ml of benzene. 130 ml of 15% butyllithium was then added dropwise to the mixture. The resulting mixture was then stirred at room temperature for 18 hours. 17.1 ml of anhydrous DMF was then dropped into the mixture, which was stirred for further 30 minutes. Then, 200 ml of 50% hydrochloric acid was added dropwise under cooling. The organic phase was then washed with 100 ml brine two times, while the aqueous phase was washed with 100 ml of methylene chloride two times. The organic phase was then dried over magnesium sulfate and the solvent was removed to give the crude aldehyde.

The crude aldehyde 5 g was then purified by column chromatography (silica gel). The product was eluted by 10% ethyl acetone/dichloromethane. The starting material and monoaldehyde were removed by 50% hexane/dichloromethane and 100% dichloromethane respectively. The yield of the dialdehyde was 3 g.

(iii) 3 g of the dialdehyde was then dissolved in 100 ml of 40% methylene/methanol and stirred overnight at room temperature. The solvent was removed to give the desired imine.

(iv) The imine obtained in the route(iii) was dissolved in 50 ml of anhydrous methanol and 2 g of sodium borohydride ($NaBH_4$) was added under cooling. The resulting mixture was stirred at room temperature for 15 hours. The solvent was removed and the solid was extracted with dichloromethane/water. The organic phase was washed with 100 ml of distilled water three times. The solvent was then removed to give the desired amine quantitatively.

(v) The 1 g of the amine as obtained in the above, 1.7 g of the bromomethyl protected boronic acid and 1 g of potassium carbonate were mixture in 100 ml of 50% acetonitrile/THF (tetrahydrofuran). The resulting mixture was refluxed overnight and filtered, and then the solvent was removed. The solid was washed with hexane and triturated with ethylacetate. Yield was 300 mg.

The percentage enantiomeric excess (ee) and optical rotation for the boronic acid product of the formula(3) are: >94% ee and $[\alpha]_D^{25}$=+12.7 (c 0.272, in methanol) for R-form (R-isomer), and >99% ee and $[\alpha]_D^{25}=-13.1°$ (c 0.4, in methanol) for S-form (S-isomer). The result of mass spectrometric analysis for both R-form and S-form of the boronic acid compound is: m/z=781[m+1] (SIMS(+), glycerol). The mass of the diglycerol boronate ester is 780.

EXAMPLE 2

Two boronic acid compounds were prepared in which $R_1=R_2=OH$ and $R_1=R_2=$ethoxy in the aforesaid general formula (2), respectively. The compounds were prepared in the manner as described in Example 1, except that step (i) was omitted for the compound of $R_1=R_2=OH$ and ethyl bromide was used in step (i) instead of methyl iodide for the compound of $R_1=R_2=$ethoxy.

The mass spectrometric analysis of the compounds showed that m/z (SIMS(+)) are 777 in the case of $R_1$ and $R_2$ being OH and 833 in the case of $R_1$ and $R_2$ being ethoxy, respectively, indicating that the desired boronic acid compounds were successfully obtained.

EXAMPLE 3

The R-isomer and S-isomer of the boronic acid compound of the formula(3) as prepared in Example 1 were measured for fluorescence in the presence of saccharides in order to evaluate characteristic properties thereof.

The R-isomer and the S-isomer were each resolved at a concentration of 0.00001M in a 33.3% methanol aqueous solution with a pH of 7.77 (buffered with 0.01M KCl, 0.002642M $KH_2PO_4$, 0.00264M $Na_2HPO_4$). To the solution were added dropwise portions of saccharide (D-glucose, L-glucose, D-fructose or L-fructose) and fluorescence intensity was measured on a Hitachi F-4500 fluorospectrophotometer with a Hewlett Pachard VETRA 286/12 computer. The wavelength for excitation is 289 nm, while the wavelength for emission is 358 nm.

Figure 2:
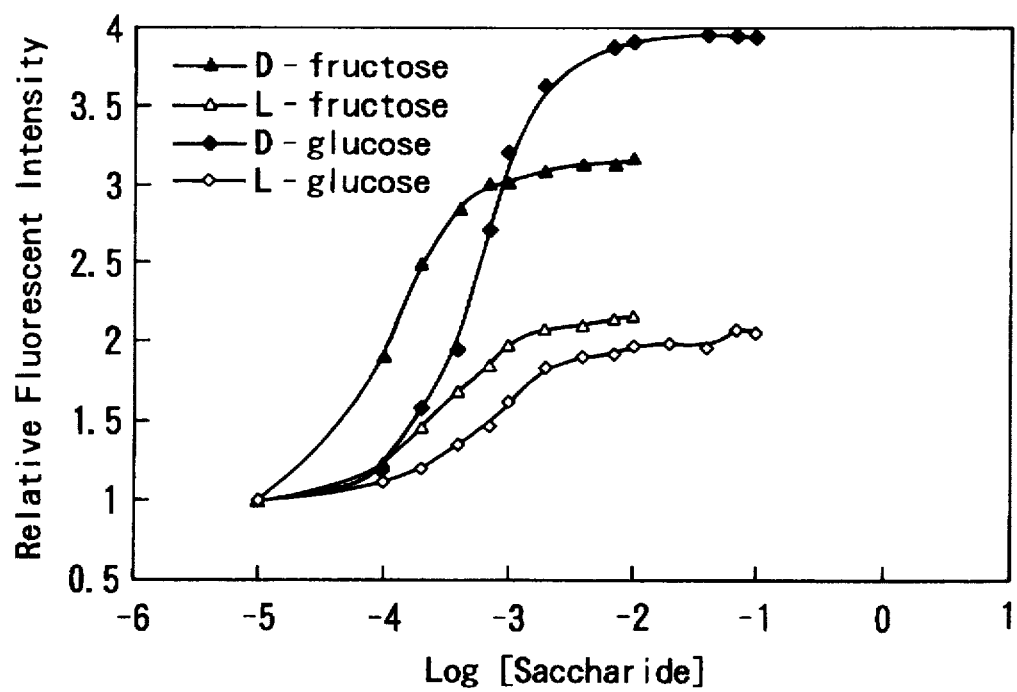
FIG. 2 demonstrates fluorescence intensities of the R-isomer of the boronic acid compound of the present invention in the presence of monosaccharides.
Figure 3:
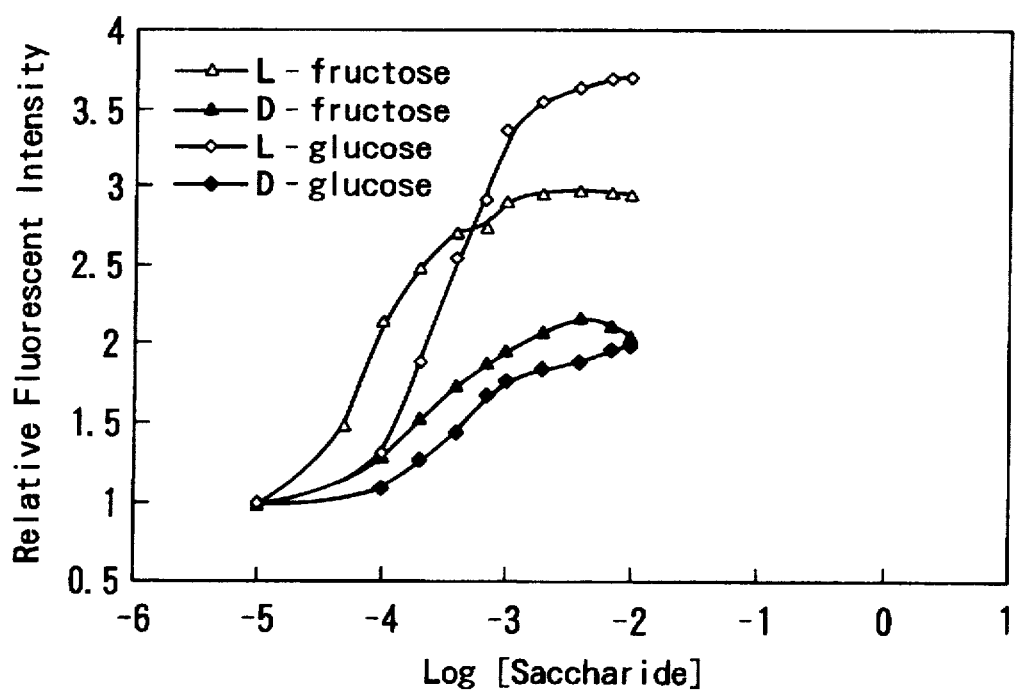
FIG. 3 demonstrates fluorescence intensities of the S-isomer of the boronic acid compound of the present invention in the presence of monosaccharides.

The results are shown in FIG. 2 for the R-isomer and in FIG. 3 for the S-isomer. As can be seen from the figures, the R-isomer exhibits much higher fluorescence intensities in the presence of D-glucose or D-fructose than in the presence of L-glucose and L-fructose (FIG. 2). In contrast, the S-isomer shows higher fluorescence intensities in the presence of L-glucose or L-fructose than in the presence of D-glucose or D-fructose (FIG. 3).

The stability constants(K) were also determined from the titration curves in terms of fluorescence intensity versus saccharide concentration assuming that a 1:1 complex is formed between the boronic acid compound and the saccharide. For R-isomers, the values of log K are 3.3 with D-glucose, 3.1 with L-glucose, 4.0 with D-fructose and 3.5 with L-fructose, all being higher with D-isomer of saccharide. For S-isomers the values of log K are 3.4 with D-glucose, 3.5 with L-glucose, 3.7 with D-fructose and 4.0 with L-fructose, all being higher with D-isomer of saccharide.

From these results it is understood that the boronic acid compound having a binaphthyl group as expressed by the formula(3) has a high selectivity to the D-isomer of a monosaccharide when it is in the form of R-isomer, while it exhibits a high selectivity to the L-isomer of the monosaccharide when in the form of S-isomer, all emitting strong fluorescence upon binding to the respective saccharide isomers.

What is claimed is:

1. A fluorescent compound of the following general formula:

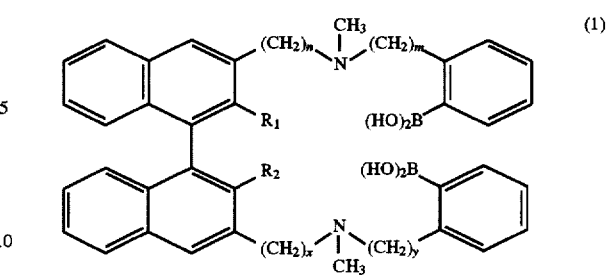

in which $R_1$ and $R_2$ are generally the same but may be different and each selected from the group consisting of alkoxy groups having 1 to 4 carbon atoms, n+m is 2 or 3, x+y is 2 or 3 in which each of n, m, x and y may be zero, and the above formula expresses either R-form or S-form of the compound.

2. A fluorescent compound of the following general formula:

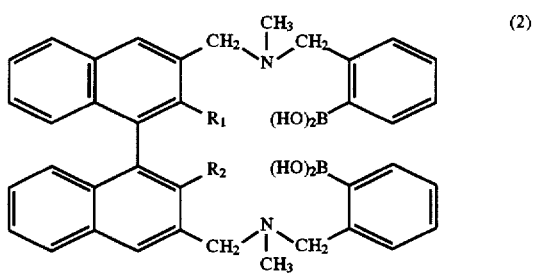

in which $R_1$ and $R_2'$ are generally the same but may be different and each selected from the group consisting of alkoxy groups having 1 to 4 carbon atoms, and the formula expresses either R-form or S-form of the compound.

3. A fluorescent compound of the following formula:

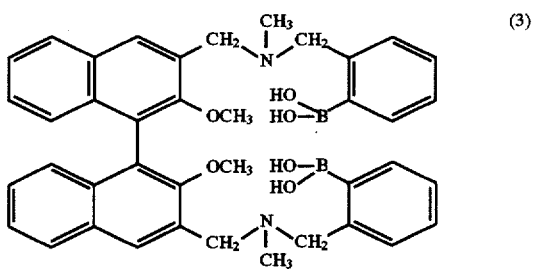

in which the formula expresses either R-form or S-form of the compound.

4. A saccharide-detecting kit comprising R-form and/or S-form of a fluorescent compound of claim 1 in a solid or crystalline state, a buffer solution and a set of standard solution, the standard solutions being ones at varied concentrations of the saccharide to be detected.

5. The saccharide-detecting kit of claim 4 wherein the fluorescent compound is the R-form of the compound of claim 3 and the kit is suitable for use in the detection of D-glucose or D-fructose.

6. The saccharide-detecting kit of claim 4 wherein the fluorescent compound is the S-form of the compound of claim 3 and the kit is suitable for use in the detection of L-glucose or L-fructose.

7. The saccharide-detecting kit of claim 4 wherein the fluorescent compound is R-form and S-form of the compound of claim 3 and the kit is suitable for the use in the detection of a racemic mixture of glucose or fructose.

* * * * *